US006585646B2

(12) United States Patent
Berlin

(10) Patent No.: US 6,585,646 B2
(45) Date of Patent: Jul. 1, 2003

(54) SCREENING TEST AND PROCEDURE USING SKIN PATCHES

(75) Inventor: Stuart Berlin, Thousand Oaks, CA (US)

(73) Assignee: Hermetic Diagnostics, Inc., Thousands Oaks, CA (US)

( * ) Notice: Subject to any disclaimer, the term of this patent is extended or adjusted under 35 U.S.C. 154(b) by 0 days.

(21) Appl. No.: 09/994,535

(22) Filed: Nov. 26, 2001

(65) Prior Publication Data

US 2002/0115921 A1 Aug. 22, 2002

Related U.S. Application Data

(60) Provisional application No. 60/250,206, filed on Nov. 29, 2000.

(51) Int. Cl.$^7$ .................................................. A61B 5/00
(52) U.S. Cl. ........................ 600/362; 600/306; 600/309; 600/573
(58) Field of Search ................................ 600/362–367, 600/306, 309, 573

(56) References Cited

U.S. PATENT DOCUMENTS

| | | | | |
|---|---|---|---|---|
| 3,552,929 A | | 1/1971 | Fields et al. ................... 23/253 |
| 4,329,999 A | | 5/1982 | Phillips ....................... 128/760 |
| 4,444,193 A | * | 4/1984 | Fogt et al. ................... 600/362 |
| 4,706,676 A | | 11/1987 | Peck .......................... 128/632 |
| 4,732,153 A | * | 3/1988 | Phillips ....................... 600/367 |
| 4,957,108 A | | 9/1990 | Schoendorfer et al. ..... 128/771 |
| 5,076,273 A | | 12/1991 | Schoendorfer et al. ..... 128/632 |
| 5,203,327 A | * | 4/1993 | Schoendorfer et al. ..... 600/362 |
| 5,441,048 A | | 8/1995 | Schoendorfer et al. ..... 128/632 |
| 5,443,080 A | * | 8/1995 | D'Angelo et al. .......... 600/573 |
| 5,445,147 A | | 8/1995 | Schoendorfer et al. ..... 128/632 |
| 5,459,080 A | | 10/1995 | Adamczyk et al. ......... 436/539 |
| 5,525,521 A | * | 6/1996 | Peranich ..................... 436/150 |
| 5,638,815 A | | 6/1997 | Schoendorfer et al. ..... 128/632 |
| 5,676,144 A | | 10/1997 | Schoendorfer et al. ..... 128/632 |
| 5,798,266 A | | 8/1998 | Quay et al. .................... 436/64 |
| 5,801,001 A | | 9/1998 | Sager et al. ................. 435/7.23 |
| 5,846,559 A | | 12/1998 | Hopp ......................... 424/448 |
| 5,895,765 A | | 4/1999 | Rheinheimer et al. ...... 436/514 |
| 6,040,194 A | | 3/2000 | Chick et al. ................. 436/501 |
| 6,042,543 A | * | 3/2000 | Warwick et al. ............ 600/362 |
| 6,063,029 A | * | 5/2000 | Saita et al. .................. 600/309 |
| 6,443,892 B1 | * | 9/2002 | Kidwell ...................... 600/362 |
| 6,479,015 B1 | * | 11/2002 | Long et al. ................... 422/58 |

* cited by examiner

Primary Examiner—Robert L. Nasser
Assistant Examiner—Patricia C Mallari
(74) Attorney, Agent, or Firm—Koppel, Jacobs, Patrick & Heybl; Michael J. Ram

(57) ABSTRACT

Marker compounds indicative of variations in physiological conditions, genetic defects or disease states have been found to be present in apocrine sweat and, in many conditions, these markers are present in apocrine sweat in elevated levels when compared to blood. These markers are collected and/or detected in apocrine sweat and used as an indicator that a disease state or particular physiological condition exists. A skin patch, wipe or electronic detector for vapors released from apocrine sweat are used to indicate the existence of a disease state or changing physiological condition. The patch or wipe can include in monoclonal antibodies or other chemical compounds that can indicate the presence of specific markers. This may include indicators that render visible, the existence of a reaction between the monoclonal antibody or chemical compound and the marker compound to indicate the existence of the condition being tested for. Various different disease states can be detected including, but not limited to heart disease, cancer, autoimmune disease, viral or bacterial disease, renal disease, drug intoxication and other systemic illnesses. Fertility for conception and histocompatibility for organ transplantation of individuals should also be detectable.

18 Claims, No Drawings

SCREENING TEST AND PROCEDURE USING SKIN PATCHES

Benefit is claimed from Provisional Application Ser. No. 60/250,206 filed Nov. 29, 2000.

The present invention relates primarily to a test for diagnosing the existence of certain disease states or physiological conditions in mammals based on the collection and analysis of apocrine sweat.

BACKGROUND OF THE INVENTION

It is known that certain disease states or variations from normal physiological conditions can be detected or monitored by analyzing body fluids for variations in constituents of those body fluids. Blood is a highly complex suspension with many elements, which can be measured and analyzed to measure normal homeostasis and variations from normality. Blood is frequently analyzed for variations of various constituents (cholesterol, glucose, etc.), as well as its cellular constituents, as indicators of possible abnormal health conditions. In a like manner, a urine analysis may be used to detect various chemical imbalances, pregnancy or the presence of various legal or illegal drugs by testing for metabolites of the target drug. In addition, there are numerous examples of calorimetric test strips, typically used on urine, for indicating various concentrations of normal fluid constituents or environmental contaminants such as various metals, glucose, protein and ketones. The strips provide a visible indication of a threshold level of normally present reference analyte such as IgG, albumin or the like.

Diagnostic studies of chemical imbalances in other body fluids, such as sweat, can also be indicative of different disease states. For example, an increase in the level of chloride ion in sweat is indicative of cystic fibrosis. U.S. Pat. No. 3,552,929 describes a band-aid type test patch for collecting perspiration. The test patch is applied to an accessible skin surface for collecting eccrine, not apocrine sweat. It is then removed and subjected to a series of analytical tests to determine the concentration of chloride ions as an indicator of cystic fibrosis. U.S. Pat. No. 4,329,999 to Phillips is a further example of a sweat collection device for the detection of drug or alcohol use. The patch was applied to shaved skin surfaces (ankle or calf) which do not have apocrine sweat glands and remained in place for ten days. U.S. Pat. No. 4,706,676 discloses a third example of a dermal patch for detecting exposure to various different environmental chemicals. No attempt was made to collect apocrine sweat.

U.S. Pat. No. 5,676,144 to Schoendorfer and related patents (U.S. Pat. Nos. 5,638,815; 5,465,713; 5,438,984; 5,441,048; 5,203,327 and 4,957,108) describe skin patches which contain various immobilized specific binding agents for certain reference analytes as well as compounds to be detected. Schoendorfer recognizes that there are both eccrine and apocrine sweat glands, that perspiration can be either sensible or insensible and that various locations on the body sweat at different rates. However, he fails to recognize the unique diagnostic function of apocrine sweat glands and proceeds to collect eccrine sweat from the chest because large quantities of sweat can be collected. After a sufficient volume of sweat is collected the patches are then removed and subjected to various different laboratory procedures to detect the presence or increased levels of various substances such as creatine kinase MB (CK—MB). CK—MB is released from cardiac muscle during myocardial infarction and other cardiac stress and therefore is an indicator of cardiac injury. As indicated in U.S. Pat. No. 5,203,327, many chemical species detectable in blood or urine, such as sodium, calcium, chloride and potassium, are also detectable in lower concentrations in sweat. Table 1 of the '327 patent also lists numerous other normally occurring components detectable in various concentrations in sweat. Affinity chemistry can be developed and incorporated in skin patches for monitoring the concentration of these various chemicals. In addition, various metabolites of drugs of abuse such as THC, morphine, cocaine or methadone can be detected in sweat. However, with the exception of colorimetric indication of a normally present reference compound, such as IgG or albumin, which is used to provide an indication that a minimum volume of sweat has entered the patch, the compounds of interest are merely collected by the patch (U.S. Pat. No. 5,203,327, col. 16, lines 4–30). Detection and analysis of the target component is then performed in a laboratory setting.

The FDA has approved sweat collection patches for use in drug abuse screening programs to test for amphetamines, cocaine, marijuana, PCP, heroin meth-amphetamines, their metabolites and other opiates. Manufacturers of these products include the Sudormed Sweat Specimen Container, made by Sudorned, of Santa Anna, Calif., the EIA Micro-Plate Assay, made by SolarCare Technologies Corporation, Bethlehem, Pa. and the PharmaChek™ Sweat Patch from Pharmachem Laboratories Inc. of Menlo Park, Calif. These patches are waterproof, adhesive pads about the size of a playing card which is worn on the back, upper arm or lower chest. As such, it collects eccrine sweat. The patch has a tamper-proof feature so it can be applied only once and not removed and reapplied later. It is not designed for use by individuals; instead it is intended for use by trained drug abuse testing professionals in clinical and rehabilitation centers. After removal, the test patch is sent to a test laboratory where the presence and quantity of the target compound is detected by a special laboratory assay. It must be worn for 5 to 14 days to collect an adequate quantity of chemicals indicative of drugs of abuse used during that period. Sweat testing for drugs of abuse provides a convenient and considerably less invasive method for monitoring drug exposure than blood or urine. Typically, ELISA immunoassay is used to detect opiates collected on the patch from eccrine sweat and GC/MS is used to determine specific opiates. For comparison urine specimens are subjected to qualitative analysis by EMIT. However, the percentage of false negative results with the patches indicates that weekly sweat testing may be less sensitive than thrice weekly urine testing in detecting opiate use. (Huestis M. A., Cone, E. J., Wong, C. J., Umbricht, A., and Preston, K. L. *Journal of Analytical Toxicology*, 24, pp. 509–521, 2000). This is most likely because those skilled in the art selected an inappropriate source of sweat (eccrine sweat), not recognizing the unique diagnostic capacity of apocrine sweat, Further, because of the extended wear requirement (up to 14 days), the ability to rapidly test for the presence of drugs using presently available sweat collection patches and procedures is not possible.

Besides the use of skin patches to collect sweat, there are also several skin patch designs for use to deliver chemicals to the skin surface, such as anti-infectives or allergens, for treating various maladies or for analyzing sensitivity to various allergens.

It is also known to collect an analyte on a test strip and then perform various tests on the analyte in a laboratory environment. U.S. Pat. No. 5,459,080 sets forth numerous prior techniques for analysis, both quantitatively and qualitatively, of the presence of various compounds found in body fluids. In particular, the use of specific binding reagents is discussed. Such analytes include, but are not limited to, antibodies, antigens, drugs and hormones. One technique for analyzing these materials, referred to as immunoassay procedures, uses antibodies and antigens, i.e. immunoreactants, which are capable of binding with each other, creating a highly specific reaction product indicative of the presence of the antigen. To use these techniques the analyte must first be collected and then transported to a laboratory where the analytical procedure can be performed. Typically, the analyte on the test strip is then contacted with an indicator reagent which is then subjected to a detection means. The requirement for such a procedure results in a major deficiency for diagnostic test strips as it is often desirable to be able to read the test strip on the patient or immediately upon removal of the test strip without performing a further analytical procedure.

Other patents directed to test strip detection systems include U.S. Pat. No. 5,900,379 to Noda et al, U.S. Pat. No. 5,965,458 to Kouvonen et al and U.S. Pat. No. 5,998,221 to Milleck et al.

In a related approach, to test for pregnancy, monoclonal antibodies are used to bind to specific chemicals, such as human chorionic gonadotropin. A detector agent is then added to the urine/antibody combination to produce a visible color change.

It is also known that certain cancers generate marker compounds, or levels of such compounds elevated above normal, which can be detected in blood and quantified. Elevated levels of prostate specific antigen (PSA) may be an indication of the presence of prostate cancer. Likewise elevated levels of prostate acid phosphatase are found in some patients with prostate cancer. The protein NPM66 is a marker for breast cancer. CA 125 is produced by a variety of cells; elevated levels are found in many women with ovarian cancer. While human chorionic gonotropin (HCG) is normally produced by the placenta during pregnancy, it can also indicate a rare form of uterine cancer. Porter-Jordan et al (*Hematol. Oncol. Clin. North Amer.* 8, May, 1993, 28–44) suggests that tumerigenesis and tumor growth can be assessed by measuring cell proliferation markers (Ki67, cyclin D1 and proliferating epidermal nuclear antigen (PCNA)). Elevated levels of urokinase plasminogen activator (upa) has been reported in patients with breast carcinomas. CA 15-3 is shed by breast tumor cells into the blood stream. While the clinical significance is not clear, the FDA has approved test kits to measure CA 15-3-like antigen for the early detection of recurrent disease in breast cancer patients. CA 27-29 is also frequently present in breast cancer patients, as well as in the blood of patients with colon, stomach, kidney, lung, ovary, pancreas, uterus or liver cancer. CA 19-9 has been identified in patients with colorectal, pancreatic, stomach and bile duct cancer. Measurement of neuron-specific enolase (NSE) has been tracked as a marker for neuroblastoma, small cell lung cancer, Wilms' tumor, and cancers of the thyroid, kidney, testicle and pancreas. Her2/neu (also known as v-erb2) is amplified in 20–30% of breast cancer patients. It is also known that a certain percentage of cancers, particularly breast cancer, are hereditary. These patients may exhibit genetic markers. Mutations of BRCA1 or BRCA2 are found in 80% of these patients and a high percentage of women with mutated BRCA1 or BRCA 2 show a greatly increased risk of developing breast or ovarian cancer. Again, these markers are detected and quantified by blood tests conducted in a laboratory setting. It must be noted that some of these markers are normally present in small amounts in healthy patents and increased levels in cancer patients while others seem to be present only when cancer is present.

U.S. Pat. No. 5,798,266 describes the analysis of mammary fluids for breast disease markers such as described in Porter-Jordan, but particularly addresses carcinoembryonic antigen (CEA), HMFG, MCA, vasopressin or cathepsin D as markers. Also, protein Ig, suggested as a breast cancer marker, has been detected in tears.

SUMMARY OF INVENTION

Many variations in physiological conditions, genetic defects or disease states result in the release or increase of specific biological and/or chemical moieties, ie., marker compounds, into body fluids, particularly blood and urine. I have now documented several of these markers are present in apocrine sweat and are present in apocrine sweat in elevated levels when compared to blood. These markers can be collected and/or detected and used as an indicator that a disease state or particular physiological condition exists. In a first embodiment, the invention contemplates a skin patch to collect sweat, the patch including monoclonal antibodies or other chemical compounds that can indicate the presence of specific markers. This may include indicators which render visible, the existence of a reaction between the monoclonal antibody or chemical compound and the marker compound to indicate the existence of the condition being tested for. In a second embodiment a wipe to collect sweat may be used instead of a patch. A third embodiment uses an electronic sensor to collect and sample vaporized apocrine sweat or aroma emitted from the apocrine sweat gland. Various different disease states can be detected including, but not limited to heart disease, cancer, autoimmune disease, infectious disease, renal disease, drug intoxication and other systemic illnesses. In particular, occult cancers of the breast, colon, stomach, pancreas, lung, uterus, prostate, bile duct and ovary and neueroblastoma as well as various forms of leukemia can be detected by this technique.

DESCRIPTION OF INVENTION

It is generally believed that human sweat has a chemical composition which reflects chemical changes in blood. In other words, when a chemical compound not normally present in blood, or a compound with cyclical presence, appears in the blood stream of an individual, it is believed that that compound, or a corresponding compound, analog, metabolite or reaction product, referred to as a by-product, of that compound which can be correlated with a systemic disease state or a change in physiological function, such as ovulation, can usually be identified in sweat of that individual. However, it has now been discovered that this is not generally so.

The human body has two different kind of sweat glands which, while having some similar functions, also now appear to have certain functions which are completely different. The eccrine sweat glands which are present over much of the body (arms, legs, feet, hands, abdomen, chest, back, forehead, etc.) excrete large quantities sweat and have a primary function of maintaining proper body temperature as a result of the cooling effect which accompanies evaporation of perspiration. On the other hand the apocrine sweat glands, which are located under the arms (the axilla) and in the pubic and mammary areas have a unique and unexpected function and morphology which is not demonstrated by the eccrine sweat glands. The morphology of the apocrine gland is very important. Every apocrine gland opens at the base of a hair cell. This means that the contents of the apocrine gland are deposited on a hair shaft and that the hair shaft acts as a saturated wick. The warm enclosed space of the under-arm provides a microenvironment which causes vaporization of the apocrine gland secretions. This vapor persists in the armpit which acts as a persistent smell chamber.

The apocrine gland also behaves differently from the eccrine sweat glands in how it responds to certain body conditions. The response to elevated prostate specific antigen (PSA) levels is an example. As set forth in Example 1 below, when the serum PSA level is normal, for example less than 1.0 ng/ml, the apocrine PSA level is essentially insignificant. However, when the serum prostate specific antigen level is abnormally elevated the PSA in apocrine sweat increases to a significantly greater extent and to a significant therapeutically abnormal range. An active transport ATP dependent mechanism takes place to concentrate PSA in the apocrine secretion. As a result of the morphology of the apocrine gland, the apocrine gland functions to saturate the hair follicle cells with PSA transmitting a message detectable by smell as a result of the PSA levels being elevated to an unhealthy level in the armpit smell chamber. With the discovery of this phenomena, readily readable tests providing an early warning of this serious medical problem can be developed.

I have now found that apocrine sweat glands contain chemicals in concentrated quantities which are also uniquely related to disease or physiological state. Such function or capacity is not demonstrated by the eccrine sweat glands. In other words, apocrine sweat emit odors or aromas and contain chemicals which can be directly correlated with disease state or the state of certain body functions which have, in the past only been determined by blood or urine tests or other more complicated diagnostic procedures. In comparison, eccrine sweat does not contain these chemical compounds or, if present, they exist in much lower concentrations. It is believed that this function is part of the normal evolutionary development of humans and provides to a second individual the capacity to sense if the first individual has a disease or body malfunction. The utilization of the function of the apocrine sweat gland as an olfactory signaling system to communicate the health or physiological status of an individual has profound implications for the understanding of evolution in humans, and presumably other animals as well. It is unlikely that the only evolutionary pressure which shaped this system is mate selection. Once the range of physiologic conditions that the apocrine gland is sensitive to is identified it may become clearer. However, the demonstration of an olfactory system to signal health status means there is an evolutionary advantage in identifying who is ill. Caring for the sick is a human trait that confers significant evolutionary advantage. It is entirely possible that humans in pre-historic times, who did not wash and hide their smells behind deodorants may have actually been better than modern man in diagnosing each other's illness.

These by-products can also be detected by instrumental means or other indicators early in the course of the disease to allow diagnosis while the disease is readily treatable. Apocrine sweat has been discovered to be the body fluid that has evolved for the purpose of communicating the health status of an individual. Also, female apocrine sweat aromas emitted during ovulation may provide a stimulation toward intercourse and procreation; male apocrine sweat aroma is sensed by a female in the selection of a suitable mate for breeding, specifically in terms of the immune system of the offspring.

Several biomarkers have been identified for breast cancer. These can be utilized in an apocrine sweat patch test to signal occult breast cancer. It is believed that anaysis of apocrine sweat will lead to the discovery of entirely new and as yet unknown biomarkers for various cancers. A patch can also be produced which can indicate the presence of more than one marker for more than one disease. Once a biomarker is identified it can be used in immunohistopathological evaluation of malignant tumors to determine its location in the tumor cell.

Once a biomarker is identified an apocrine sweat diagnostic modality, using the teachings herein, can be established. This will result in a diagnostic screening test using the patch and then a secondary confirmatory test can be performed to locate the tumor in the body.

The availability of an apocrine test patch incorporating markers identified as indicative of breast cancer can supplement or be used as a prescreen for mammogram. It is expected that there will be a number of individuals considered by mammography to be normal who will actually have occult breast cancer. These instances, when detected by an apocrine skin patch, should not be considered as false positives for breast cancer but instead an early warning of the future appearance of the disease. Mammography is limited in its ability to detect very small or dispersed tumors. However, tumors of any size generate biological markers, which will be present in the blood and concentrated in the apocrine sweat. The presence of the marker is indicative of an abnormal physiological state whether or not such condition can be determined by other presently available less sensitive diagnostic modalities. Breast cancer now occurs in one out of nine women and is generally considered to have been present for five or six years before presentation (detection by present detection modalities). It is generally accepted that a mammogram has limited sensitivity and that there are individuals who have occult breast cancer that the mammogram will not detect.

EXAMPLE 1

The superior and unexpected diagnostic utility of apocrine sweat collection and analysis in cancer detection is demonstrated by the analysis for PSA in apocrine sweat when compared to eccrine sweat or blood. Approximately 0.5 cc of eccrin sweat, apocrine sweat, and blood of two individuals was tested for PSA. One individual had normal PSA blood levels while the other had significantly elevated blood PSA. Values for PSA in blood, eccrine sweat and apocrine sweat are as follows:

|  | PSA level (ng/ml) | | |
| --- | --- | --- | --- |
|  | eccrine sweat | apocrine sweat | blood |
| RK | 0.34 | 10.3 | 3.91 |
| SB | 0.08 | 0.16 | 0.92 |

RK has an abnormally high blood PSA level. This was reflected in a significantly greater quantity of PSA in apocrine sweat and a 29.4 to 1 ratio of PSA in apocrine compared to eccrine sweat. Still further, PSA is elevated in apocrine sweat when compared to blood with a 2.6 magnification of PSA in apocrine sweat. This means that there is an active process taking place in the apocrine gland to increase the concentration in the sweat produced by the apocrine gland. In the normal individual there is more PSA in apocrine than eccrine sweat but the ratio is not as pronounced, and there is no concentration over that in blood. It can also be seen that the amount of PSA in eccrine sweat is significantly lower than in blood (a dilutive effect) and the increase in the amount of PSA in eccrine sweat remains in proportion to the increase in blood. However, the increase in PSA in blood is reflected by a significantly greater increase in apocrine sweat (a magnifying effect).

Another diagnostic patch for use in indicating a disease presence contemplated by the invention is for the detection of abnormal levels of creatine phosphokinase (CPK). CPK is an enzyme that is present in all human muscle tissue. However, there are subtypes of this enzyme of which CPK-MB is the subtype that is present in cardiac muscle. When there is damage to cardiac muscle the cells leak CPK-MB. This is used to evaluate individuals who present with chest pain. Serial blood samples are typically drawn to see if CPK-MB (and also other enzymes) become elevated in serum over a period of time. While this test has significant diagnostic value, it has the disadvantage that the results take an unacceptable time to generate, which is critical when an individual is having a heart attack. CPK-MB is very similar to PSA as a biomarker in that it is associated with a specific kind of cell (cardiac muscle cell compared to prostate cell). It is believed that it can be readily and rapidly detected and measured in apocrine sweat as the CPK-MB should also be elevated in apocrine sweat when CPK-MB is elevated in serum. This is supported by anecdotal stores of dogs able to determine that his master is ill and thus saving his master's life. In reported incidents, tests confirmed that the man had coronary artery disease and was able to be treated in a timely manner. However, it was the keen sense of smell of the dog that detected that something was wrong. Based on applicant's testing it is believed that the dog was able to detect CPK-MB in his master's apocrine sweat by his sense of smell.

Since CPK-MB is a known chemical entity, the invention contemplates an apocrine sweat collection patch incorporating a reactant chemical or biological material sensitive and specific to concentrations of CPK-MB in excess of predetermined threshold levels, preferably containing a color generating compound which can be correlated with CPK-MB presence. This device would have considerable value as a rapid, early screening tool for patients complaining of chest pain. Since these patients are often diaphoretic (sweating profusely) such a device could be used by emergency medical pers An added value of a CPK-MB apocrine patch test would be in diagnosing onnel even before the patient reaches the emergency room of a hospital to warn medical staff of likelihood and severity of a heart attack. This test patch also offers tremendous advantage for home use and could result in much earlier diagnosis than currently available.

Unfortunately for mortality from coronary artery disease, most individuals are asymptomatic until their cardiac disease presents as death. An added value of a CPK-MB apocrine patch test would be in diagnosing asymptomatic individuals. Individuals who secreted CPK-MB during exercise using the patch could be identified as having occult coronary disease. Ultimately this would be most useful for individuals at home participating in weekend exercise activity who could then place an apocrine CPK-MB patch on their armpits while exercising. A positive result during exercise would then diagnose a cardiac condition while the individual can still do something about it.

It must be recognized that all chemicals found in the body may not be markers of a disease. One example is the various chemicals generated in an individual suffering from diabetes. Example 2 reports an analysis of various compounds found in elevated levels in a diabetic individual at a point where the blood sugar levels are under control.

EXAMPLE 2

|  | Blood Serum | Eccrine | Apocrine | Normal |
| --- | --- | --- | --- | --- |
| Sodium (mEq/l) | 138 (N) | 119 (VL) | 127 (L) | 135–149 |
| Potassium (mEq/l) | 4.2 (N) | 65.0 (VH) | 69.2 (VH) | 3.5–5.2 |
| Chloride (mEq/l) | 99 (N) | 80 (L) | 96 (N) | 98–108 |
| $CO_2$ (mEq/l) | 25 (N) | 2 (VL) | 21 (N) | 22–32 |
| Glucose (mg/dl) | 121 (H) | 52 (L) | 22 (VL) | 61–114 |
| BUN (mg/dl) | 60 (H) | 437 (VH) | 401 (VH) | 6–25 |
| Creatinine | 2.4 (H) | 2.2 (H) | 2.2 (H) | 0.6–1.5 |

(VL = Very low; L = Low; N = Normal; H = High; VH = Very High)

Standard analysis indicates that both eccrine sweat, apocrine sweat and blood have about the same values for the various analytes with the exception of BUN that the body must excrete, and glucose which the body must conserve. However, apocrine BUN levels can be readily used to signal an abnormally high concentration. Apparently a marker for diabetes was not identified or, because glucose was near normal, no marker was magnified in apocrine sweat. The conclusion that can be reached from this data is that a proper marker has not been identified. It can not be concluded that apocrine sweat is not a suitable test solution for diabetes. The results may be significantly different if glucose is significantly elevated.

This effect is not limited to cancer marker detection or detection of markers generated by other disease states. An apocrine response is seen when an individual consumes a drug not normally present in the body.

EXAMPLE 3

Samples of aprocrine and eccrine sweat were collected prior to oral consumption of a THC containing product. No THC was detected in either sample. The test individual then orally consumed (smoked) a quantity of a THC containing product. Small quantities (0.5 cc) of apocrine and eccrine sweat was separately collected over a period of 30 minutes under ambient conditions to induce sweating. When the collected samples were tested using standard laboratory tests for THC metabolites no detectable levels were found in either sample. However, samples tested for THC (rather than metabolites) using standard laboratory tests showed the following significant differences between eccrine and apocrine sweat, compared with THC concentrations in blood and urine.

|  | Blood | eccrine | apocrine | urine |
| --- | --- | --- | --- | --- |
| Delta 9 THC (nanograms/ml) | 21 | 4 | 107 | undetectable |

The quantity of THC in apocrine sweat was significantly greater than in eccrine sweat (26.75 times) and blood (5.1 times).

The unique diagnostic capability of apocrine sweat has been demonstrated with at least three distinctly different biomarkers capable of indicating an abnormal physiological condition. PSA, THC, and urea nitrogen, have been found to be subject to active ATP transport with concentration in apocrine sweat. These markers, disease related biochemicals or indicators of compromised normal physiological condition are indicative of three different, unrelated physiologic situations, namely prostate cancer or benign prostatic hypertrophy, chronic renal failure, marijuana and opiate intoxication. These are merely representative of the disease state or physiological condition which can be signaled by functioning of the apocrine gland through the release of detectable marker constituents present in the smell chamber. Collection, analyzing or signaling abnormal constituents of apocrine gland output by collecting aroma samples (vaporized apocrine gland secretions), clinical laboratory analysis of dissolved or vaporous components of apocrine sweat, or the in situ signaling of presence of selected target components by, for example, antibody detection techniques and/or colorimetric indicators now becomes possible in a highly reproducible and specific manner. As such the false positive and false negative results obtained by the general and indiscriminate collection of sweat, resulting from the failure of prior techniques to recognize the difference between eccrine and apocrine sweat, can be eliminated. Collection of only apocrine sweat now renders useful, for use in many clinical situations and drug testing, what was previously an unreliable technique.

The techniques and inventive procedures reported herein are based upon the testing of liquid apocrine sweat as a highly indicative media when compared to liquid eccrine sweat and blood or urine. An the apocrine sweat can be collected on a moisture absorbing patch adhered to the collection site to receive apocrine sweat followed by a detection or visible indication. Alternatively, topically pad or wipe can be used to collect, in a rapid manner, the sweat that is on the surface of the axillary (under arm) or groin hairs (ie, collect apocrine sweat). Chemical or monoclonal antibody detection systems can then be used to identify specific chemicals or biomarkers in apocrine sweat associated with specific disease states or body functions.

However, another methodology is the use of electronic aroma or smell detector systems, referred to as an electronic nose, to take advantage of the discovery of specific function of the apocrine gland. Examining the vaporized apocrine gland secretions using such devices provides a new diagnostic modality which is rapid, sensitive and non-invasive. It also has the advantage of evaluating the product of the apocrine gland in the form (vapor) intended.

Research reported by others has documented the excretory function of eccrine sweat. Urea nitrogen and creatinine have now been documented to have substantially the same values in both apocrine and eccrine sweat in chronic renal failure. Both urea nitrogen and creatinine are toxins and there is an obvious advantage to eliminating them from the body by rapid perspiration. However, the volume of apocrine sweat is minimal compared to eccrine sweat and can not remove a significant amount of any chemical from the body. It is therefore interesting to note that the body does not respond to delta nine tetrahydrocannibinol as a toxin. It remains to be seen whether all foreign chemicals which are administered to the body are treated as toxins by the eccrine sweat glands, or whether their presence will just be signaled solely or primarily by the apocrine glands. Active transport concentration has only been demonstrated to be shared with both apocrine and eccrine glands with urea nitrogen. Creatinine is also interesting in that the values of both eccrine and apocrine gland secretions in Example 2 above were just below that of serum values, 2.2 compared to 2.4. This is clearly different from the situation of beta HCG (see below) or PSA in the normal range where the values of both eccrine and apocrine gland secretions were minuscule compared to serum values. Creatinine excretion in sweat demonstrates that there is a situation where a chemical may be excreted in eccrine sweat or signalled in apocrine sweat with concentrations that are less than but approaching serum levels. This is different from the biomarkers described above which are concentrated by active transport but which still may have significant clinical application for diagnostic purposes.

It has been documented that ovulating women were able to identify the histocompatability type of men by using the smell deposited upon t-shirts that were saturated with their sweat. Based on the laboratory data regarding the ability of women to detect histocompatibility of males from apocrine sweat, it is believed that comparative analysis of apocrine sweat of multiple individuals, either electronically or chemically, can be used to identify an individual's histocompatibility type. Ehere this type of testing is used in transplant medicine for screening organ donors for a possible histocompatible match, the ability to match donors using apocrine swaet analysis can be significant.

Also, based on the data listed herein for other compounds concentrated in apocrine sweat it is expected that the apocrine gland secretion of a pregnant woman will not reflect an abnormal condition, pregnancy not being a condition requiring a biological alert. This is confirmed by analysis that shows beta HCG blood levels in a pregnant women to be 1944 $\mu$gm/ml but the levels in eccrine and apocrine sweat to be 2 and 6 $\mu$gm/ml respectively. However, ovulating women should have elevated levels of a marker, such as luteinizing hormone which triggers ovulation, or other compounds, such as estrogen known to be elevated in blood to evidence a state of fertility suitable for conception, this being a physiological state that a female body is desirous of transmitting to a male. On the other hand, significantly low levels of estrogen and/or progesterone prior to menstruation, often suggested as triggering physiological and psychological disturbances, referred to as premenstrual syndrome (PMS), could also be signaled by absence of these markers in apocrine sweat.

Specific Applications for the test modality described herein include testing of apocrine sweat for cancer markers such as elevated PSA serum levels or other cancer markers. This may be both a diagnostic tool for detecting the presence of prostate cancer and an early warning of a potential disease state. Based on data collected it is believed that the apocrine concentration of PSA, or other cancer markers, in normal individuals will reflect (be proportional to) the concentrations in blood serum. However, at a threshold level, not yet determined, which the body recognizes as abnormal, the ratio of PSA in apocrine sweat, when compared to blood or eccrine sweat will increase significantly. This can be readily detected with a simple patch or wipe collection device or electronic nose or other electronic sensor as described herein.

The invention also contemplates the utilization of an apocrine sweat collection patch which will include a reactive marker, for example sensitive to PSA levels, other cancer markers, or other disease markers in excess of a threshold level, which is the point where the apocrine gland starts to concentrate PSA.

The invention herein contemplates applicability to many other known, or presently unknown, biomarkers which can be applied to an apocrine sweat collection patch. It is expected that analysis of apocrine sweat will identify prsenetly unknown biomarkers for many cancers or other illnesses. These biomarkers will have diagnostic value both in the testing of apocrine sweat as well as expanding the utility of analysis of other body fluids such as blood and urine. For example, the patch could be used as a diagnostic test for HIV, the virus that causes AIDS. Because AIDS is a readily treatable disease, particularly if detected early, that early identification is very important. A very effective blood test already exists which looks for the presence of antibodies against HIV. This antibody, if it is in the blood should also be in apocrine sweat in elevated levels. A rapid patch test, using the technology that is used in blood testing, is therefore contemplated. The advantages of a rapid apocrine sweat test compared to blood are many. Many individuals who would not readily submit to a blood test would accept such a non-invasive test. Also, since the result would be rapid there would be no delay, as is common with blood test, to obtain an indication of a potential disease state. The test patch could be available as an over-the-counter product from a pharmacy for self administration in the privacy of a users home. It could also be used privately by an individual to test their sexual partners prior to becoming intimate. It is also likely that an antibody present in the blood in response to a bacterial or viral vector, such as anthrax, could be readily and rapidly detected in apocrine sweat. This could provide a modality to differentiate between viral and bacterial illness and therefore make the clinical decision to use antibiotics more scientifically based.

In several disease modalities contemplated by the invention, it is possible that this test can be further accelerated by applying the patch and then stimulating the patient to sweat by a standard exercise protocol or by placing the patient in a room with an elevated temperature, or even a sauna.

Screening studies described above indicate that the technique and devices described herein have broad utility and are not limited to the specific examples set forth. It is anticipate that there are many biomarkers that are as yet unidentified but which are present in apocrine sweat in various abnormal physiological conditions (Alzheimer's, stoke, Parkinson's, various cancers other than prostate or breast cancer, or which reflect changing body functions (ovulation, PMS, pregnancy or fetal stress during pregnancy) that are susceptible to identification or indication by apocrine sweat detection.

A skin patch incorporating features of the invention would comprise a sensor portion which includes one or more marker sensitive chemicals or antibodies (a detector chemical) and a visible agent incorporated therewith which will indicate that the detector chemical has reacted with or become bound to the by-product, referred to as an indicator patch or wipe. The patch could also include means to attach it to the skin surface such as an adhesive strip. Any of numerous prior known skin patch constructions can be used. The invention is not directed to the specific design or use of a skin patch to collect body chemicals. Instead it is directed to a method of detecting cancer, other disease states, or physiological conditions by placing a skin patch, using a wipe, or applying an electronic sensor which detects and identifies vaporizing apocrine sweat so as to collect emissions (liquid or vapors) from the apocrine sweat gland. The wipe or patch can have a detector specific to one or more compounds present in apocrine sweat which are only present, or are present in significant elevated levels, when that condition being diagnosed for exists. The patch, wipe or detector may be combined with an agent which provides a visible indication, such as a color change, when the compound exists in collectable and measurable quantities in apocrine sweat. It is contemplated that the visible indicia of the presence of a target compound can be ascertained while the patch is still attached to the skin (ie, by viewing the outer surface of the patch) so that a time dependent response can be monitored or, alternatively, immediately upon removing the patch and observing the skin contacting surface of the patch. Still further, the invention contemplates that the agent which provides a visible indication of marker presence can be applied to the patch or wipe immediately prior to collecting the sweat or immediate after the sweat is collected.

The skin patch would be applied to a portion of the body where apocrine sweat is generated, such as the underarm or groin, so as to require the shortest period of time to collect an adequate sample of sweat. Topical or systemic compounds which stimulate the generation of perspiration can also be used to increase the generation of sweat. Alternatively or in addition to these compounds, exercise sufficient to increase sweat may also be useful to increase sweat production and reduce the time to collect a sufficient quantity of sweat. Because the technique and device described herein is non-invasive it may have particular utility in acute or urgent care facilities or in instances where blood samples are difficult to obtain or diagnose, such as in pediatrics or rural and third world settings. While the technique and products set forth herein are primarily intended for use in humans, there is no reasons why the same product and technique can not be adapted for use on other mammals which produce sweat or other skin exudates, the techniques also be applicable in a veterinary setting.

While the principal embodiments are directed to substances generated by the apocrine gland which are analyzed or detected contemporaneously with the collection of such materials, the invention does not exclude the collection for remote primary or secondary analysis. By secondary analysis, applicant contemplates the generation of a s signal, upon collection of the apocrine gland sweat, that a target substance has been detected followed by a laboratory analysis of the collected substance to specify and/or quantify the collected substance. Further, while apocrine sweat has been identified as a unique source of particular markers, it is also known that eccrine sweat may have the same markers but in lower concentrations. The indicator patch or wipe therefore can also be utilized in the same manner on eccrine sweat, even though such use may be less efficient or effective.

It is evident from the foregoing that there are many additional embodiments of the present invention which, while not expressly described herein, are within the scope of this invention and may suggest themselves to one of ordinary skill in the art. For example, It is therefore intended that the invention be limited solely by the appended claims.

I claim:

1. A method of diagnosing a disease state or physiological condition in a living mammal comprising collecting liquid or vapor components of apocrine gland secretions and providing means at a point of collection for indicating a presence of a marker compound in those apocrine gland secretions wherein the means of indicating the presence of the marker compound in the apocrine gland secretions comprises electronic sensors which indicate the presence of specific marker compounds.

2. A method of diagnosing an individual for the use of drugs comprising collecting liquid or vapor components of apocrine gland secretions and providing means for indicating a presence of a chemical component or metabolite of the drug in those apocrine gland secretions wherein an absorbent material placed against an underarm, groin or mammary area skin of the mammal collects the apocrine gland secretions, the absorbent material containing a visible indicator responsive to a chemical component or metabolite of the drug and, after a sufficient collection period, observing a color change to detector compounds caused by the presence of the chemical component or metabolite in or on the absorbent material wherein the color change is viewable only after removing the absorbent material from the skin surface.

3. A method of diagnosing an individual for the use of drugs comprising collecting liquid or vapor components of apocrine, gland secretions and providing means for indicating a presence of a chemical component or metabolite of the drug in those apocrine gland secretions comprising collecting the apocrine gland secretions by wiping an underarm, groin or mammary area skin of the mammal with an absorbent patch and observing color changes to detector compounds in or on the absorbent material.

4. The method of claim 3 comprising applying an indicator compound to the absorbent material after collection of the apocrine gland secretions to provide a color change viewable when the indicator compound reacts with a chemical compound or metabolite of the drug in the collected apocrine gland secretions.

5. A method of diagnosing an individual for cardiac disease comprising collecting liquid or vapor components of apocrine gland secretions and providing means for indicating a presence in the apocrine gland secretions of a marker compound indicative of cardiac disease wherein by an absorbent pad placed against an underarm, groin or mammary area skin of the mammal collects the apocrine gland secretions, the absorbent pad containing a visible indicator indicative of the presence of the marker compound and, after a sufficient collection period, observing a color change to detector compounds in or on the pad wherein the color change is viewable only after removing the pad from the skin surface.

6. A method of diagnosing an individual for cardiac disease comprising collecting liquid or vapor components of apocrine gland secretions and providing means for indicating a presence in the apocrine gland secretions of a marker compound indicative of cardiac disease comprising collection the apocrine gland secretions by wiping the skin of an underarm, groin or mammary area of the mammal with an absorbent pad and; observing color changes to detector compounds in or on the pad.

7. The method of claim 6 comprising applying an indicator compound to the wipe after collection of the apocrine gland secretions to provide a color change viewable when the indicator compound reacts with a marker compound in the collected apocrine gland secretions.

8. A method of diagnosing an individual for cardiac disease comprising collecting liquid or vapor components of apocrine gland secretions and providing means for indicating a presence in the apocrine gland secretions of a marker compound indicative of cardiac disease comprising sensing the cardiac disease marker in the apocrine gland secretions using electronic sensors which indicate the presence of specific marker compounds.

9. A method of diagnosing a disease state or physiological condition in a living mammal comprising collecting liquid or vapor components of apocrine gland secretions and providing means at a point of collection for indicating a presence of a marker compound in those apocrine gland secretions comprising collecting components of the apocrine gland secretions by positioning against the skin of an underarm, groin or mammary area of the mammal an absorbent patch and, after a sufficient collection period, observing a visible appearance change to detector compounds in or on the patch, said appearance change being related to the marker compound wherein the visible appearance change is a color change viewable only after removing the patch from the skin surface.

10. A method of diagnosing a disease state or physiological condition in a living mammal comprising collecting liquid or vapor components of apocrine gland secretions and providing means at a point of collection for indicating a presence of a marker compound in those apocrine gland secretions comprising collecting components of the apocrine gland secretions by wiping an underarm, groin or mammary area skin of the mammal with an absorbent patch and observing a visible appearance change to detector compounds in or on the patch, said appearance change being related to the marker compound.

11. The method of claim 10 wherein an indicator compound is applied to the wipe after collecting components of the apocrine gland secretions to provide a color change viewable when the indicator compound reacts with the marker compound in the collected components of the apocrine gland secretions.

12. A method of diagnosing a mammalian body for an existence of cancer comprising collecting liquid or vapor components of apocrine gland secretions and providing means at a point of collection for indicating a presence of a cancer marker compound in those apocrine gland secretions.

13. The method of claim 12 comprising sensing the cancer marker in the apocrine gland secretions using electronic sensors which indicate the presence of specific cancer marker compounds.

14. The method of claim 12 comprising collecting components of the apocrine gland secretions by positioning against the skin of an underarm, groin or mammary area of the mammal an absorbent patch, said patch containing at least one detector compound reactive with the cancer marker and, further comprising, after a sufficient collection period, observing a color change to the detector compound in or on the patch caused by the presence of the marker compound.

15. The method of claim 14 wherein the color change is viewable without removing the patch.

16. The method of claim 14 wherein the color change is viewable after removing the patch from the skin surface.

17. The method of claim 12 comprising collecting components of the apocrine gland secretions by wiping the skin area of an underarm, groin or mammary region of the mammal with an absorbent patch and, observing color changes to marker reactive detector compounds in or on the patch.

18. The method of claim 17 wherein an indicator compound is applied to the wipe after collecting the apocrine gland secretions to provide a color change viewable when the indicator compound reacts with a marker compound in the collected apocrine gland secretions.

* * * * *